United States Patent [19]

Wickham

[11] 3,985,142
[45] Oct. 12, 1976

[54] DEMAND HEART PACER WITH IMPROVED INTERFERENCE DISCRIMINATION

[75] Inventor: Geoffrey Gordon Wickham, Lane Cove, Australia

[73] Assignee: Telectronics Pty. Limited, Australia

[22] Filed: Jan. 14, 1975

[21] Appl. No.: 540,973

[52] U.S. Cl. .......................................... 128/419 PG
[51] Int. Cl.² .......................................... A61N 1/36
[58] Field of Search ................. 128/2.05 R, 2.06 A, 128/2.06 F, 2.06 R, 419 P, 419 PG, 419 PT, 421, 422, 423

[56] References Cited
UNITED STATES PATENTS

| | | | |
|---|---|---|---|
| 3,171,892 | 3/1965 | Pantle .......................... | 128/2.05 R |
| 3,431,912 | 3/1969 | Keller, Jr. ..................... | 128/419 PG |
| 3,661,157 | 5/1972 | Fyson et al. .................. | 128/419 PG |
| 3,759,266 | 9/1973 | Lee .............................. | 128/419 PG |

*Primary Examiner*—William E. Kamm
*Attorney, Agent, or Firm*—Flehr, Hohbach, Test, Albritton & Herbert

[57] ABSTRACT

A heart pacer providing heart stimulating electrical impulses in the absence of naturally occurring heartbeats, together with means to prevent inhibition of the electrical impulse in the presence of electrical interference signals of either physiological or nonphysiological origin. Logic functions are incorporated to detect the presence of any sensed signal occurring after a first predetermined time but earlier than a second predetermined time, both measured from the preceding detected signal which may be either a natural heartbeat, a stimulating electrical impulse, or an interference signal. The first predetermined time interval is greater than the time duration of the electrical manifestations of a single heartbeat while the second predetermined time interval is less than the interval between two natural heartbeats. Sensed signals are delayed before triggering the demand function. Upon detection of one or more signals after the first time interval but prior to the end of the second, a latch is activated to disable the inhibit function before that function can be triggered by the interference signal. The latch is held active until deactivated after a predetermined time period or until the next heart stimulating impulse is delivered.

18 Claims, 3 Drawing Figures

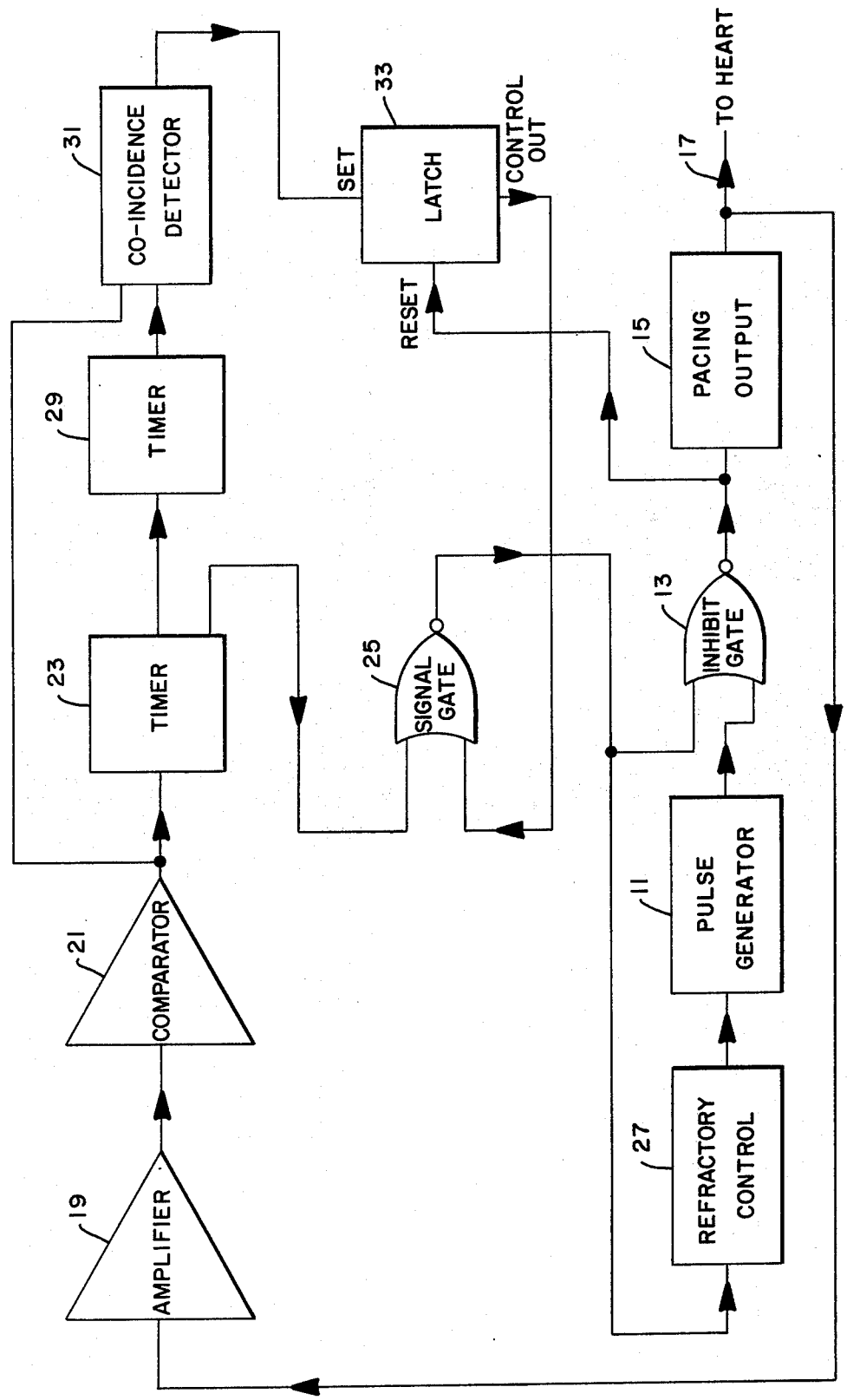
FIG.—1

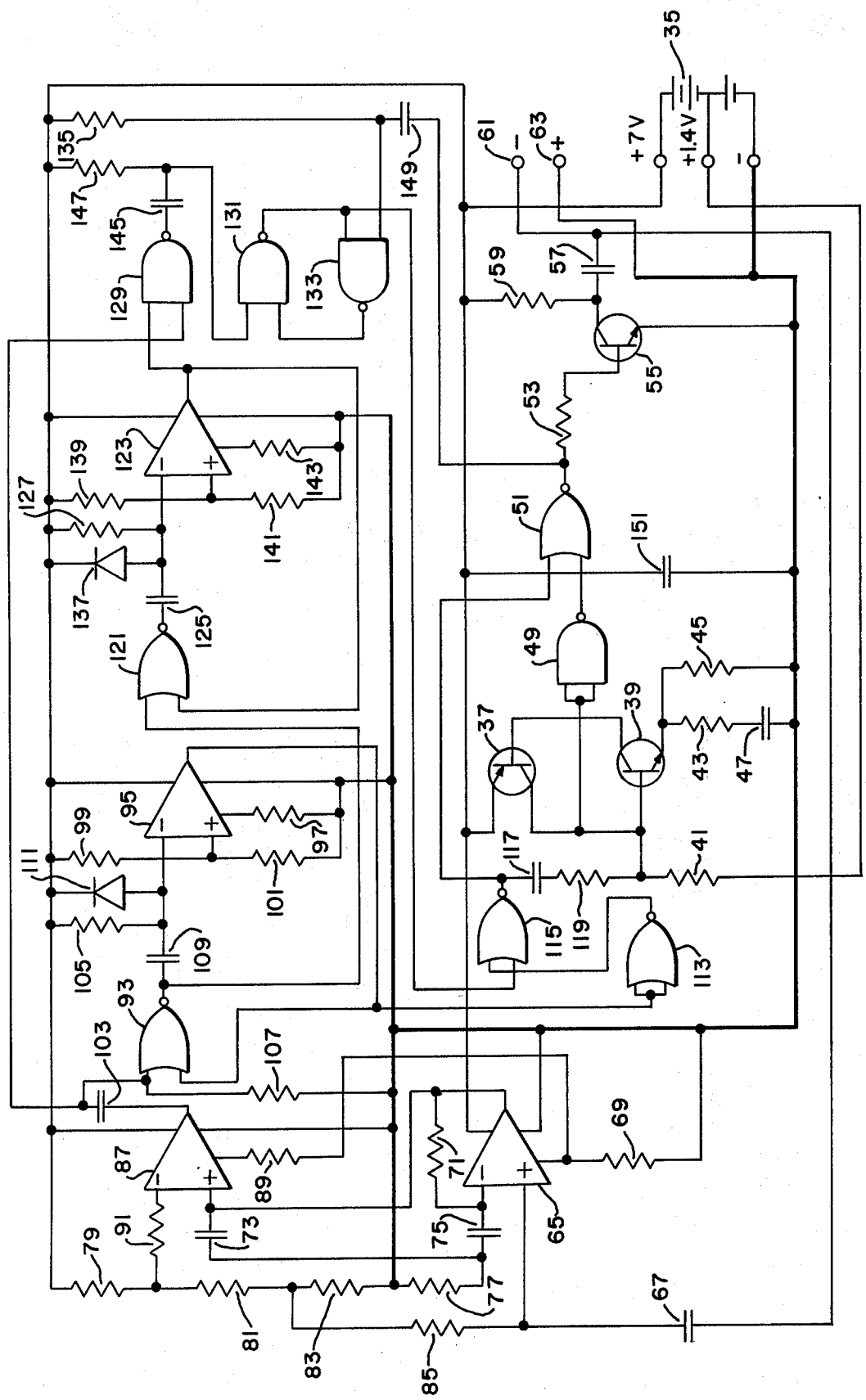
FIG.—2

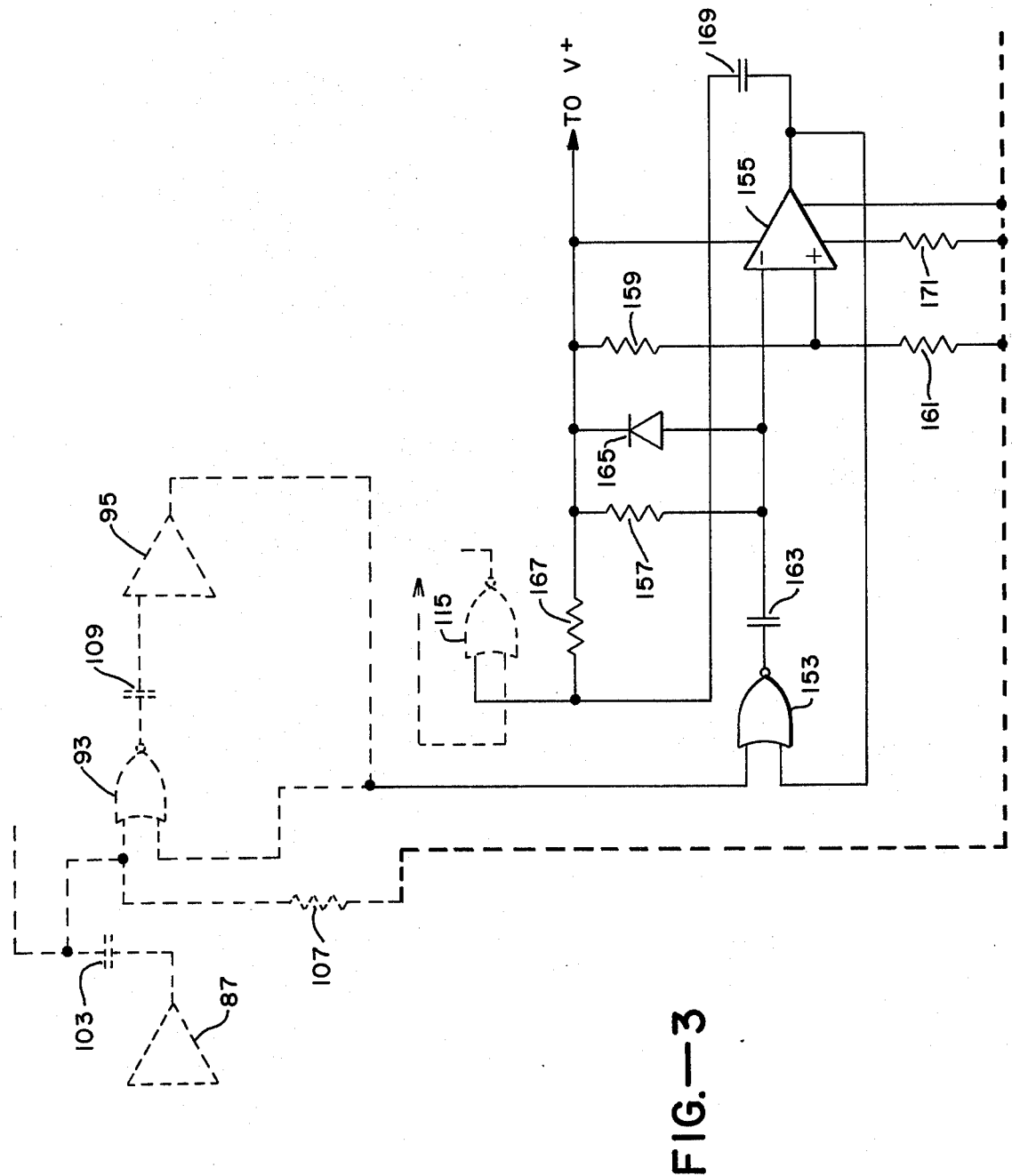
FIG.—3

DEMAND HEART PACER WITH IMPROVED INTERFERENCE DISCRIMINATION

BACKGROUND OF THE INVENTION

The invention relates to demand cardiac pacers and particularly to a pacer in which the probability of inhibition of one or more heart stimulating impulses by interfering electrical signals is substantially reduced whether those interfering signals are physiological or non-physiological in origin.

The term "demand pacer" describes that particular type of pacer in which an electrical impulse generator is connected by wires and electrodes to the heart of the patient such as to deliver pulses of a heart stimulating mangitude at a rate approximately of a normal heart beating rate. In addition, the demand pacer includes an electrical amplifier connected also to the heart and having its parameters such that it is sensitive to the electrical manifestations of a heartbeat. Upon sensing a heartbeat by the amplifier further circuitry is activated to produce a triggering impulse which is delivered to the pacing pulse generator circuit to reset the timing cycle of the pulse generator and to inhibit the generation of the next otherwise delivered heart stimulating impulse. Such a pacer is described in U.S. Pat. No. 3,345,990, issued Oct. 10, 1967 to B. V. Berkovitz for "Heart-Beat Pacing Apparatus".

In a variation of the demand pacer the action of resetting the pacing pulse generator timing cycle upon detection of a natural heartbeat is accompanied by the delivery to the heart electrodes of a pulse of heartbeat stimulating magnitude which, being synchronous with a natural heartbeat, evokes no response. This variant is commonly described as a "ventricular synchronous demand pacer". Although offering physiological benefits similar to the first described type it has a disadvantage of wasting battery energy by supplying heart stimulating impulses when not needed.

In a further variation of the demand pacer, originated by applicant and incorporated in commercial designs since 1970, the action of resetting the pacing pulse generator upon detection of a natural heartbeat is accompanied by delivery to the heart electrodes of a pulse of less than heartbeat stimulating magnitude. This further variant allows the cardiologist to recognize normal pacer sensing actions in the presence of continuous natural heartbeats without waste of battery energy consequent to the ventricular synchronous demand pacer.

All these variations come within the definition of a "demand pacer", to which the present invention relates, although it must be pointed out that the response to electrical interfering signals is not normally the same in each of these variations. In the demand pacer in which sensed heartbeat produces resetting of the pacing pulse generator without coincident delivery of an impulse to the heart, the sensing of electrical interfering signals can cause complete suppression of the pacing function in the absence of natural heart rhythm — a life threatening situation.

In the ventricular synchronous demand pacer, in which an impulse of heart stimulating magnitude is delivered to the heart electrodes upon sensing a natural heartbeat, the sensing of electrical interfering signals can cause a speed up of the rate of delivery of heart stimulating impulses and a consequent physiologically abnormal heart rate — again, a life threatening situation. Thus, it can be seen that it is essential to minimize or eliminate the probability that any given interfering electrical signal might cause maloperation of a demand pacer.

To this end, prior art pacers have provided for tuning the demand sensing amplifier such as to make it most sensitive to those frequencies contained within that electrical manifestation of a naturally occurring depolarization of the cardiac muscle cells commonly described in clinical practice as the QRS sector of a cardiogram. Conversely, it is tuned to be less sensitive or insensitive to frequencies outside the QRS spectrum. The spectrum lies between approximately 20 Hz. and 100 Hz. with the frequency of peak energy density varying considerably from subject to subject.

With the tuning it is, of course, possible to eliminate the effect of interfering signals having frequencies outside the spectrum if of moderate magnitude. However, interfering signals can be of a magnitude many times greater than the heart's QRS signal and thus penetrate the tuning of the sensitive amplifier even when not containing frequencies within the amplifier's tuned spectrum.

Additionally, common sources of electrical interference produce frequencies within the amplifier's tuned spectrum. Included among these are sources of 50 Hz. to 60 Hz. power means, arc producing devices, such as welders or commutator machines, and other muscles of the body. Additionally, the interfering signals may not be a continuous wave of one discrete frequency but may contain many frequencies or be comprised of periodic or non-periodic short bursts of interference. As stated earlier, suppression of the heartbeat pacing impulses of a demand pacer by interfering signals is a life threatening event where the patient's heart is not beating in a natural rhythm at the time. Similarly, acceleration of the heartbeat pacing impulses is life threatening, irrespective of whether the patient has a natural heart rhythm at the time. In contrast, it is generally agreed that a situation in which the pacer delivers heart stimulating impulses at its preset rate even in the presence of naturally occuring heartbeats, can be tolerated by most patients for short periods.

There has been provided in the prior art designs such that the heart pacing impulses of the demand pacer are not suppressed or accelerated in rate (depending upon the form of the variation) but continue to be delivered at the preset rate even in the presence of certain forms of interference. Should the patient, at that time, have a natural heart rhythm, there will occur competition between the natural heart rhythm and the pacer stimulating rhythm. However, as previously stated, this is tolerable in a short term and unquestionably preferable to the life threatening alternative.

Examples of such prior art are two U.S. patents in the name of B. V. Berkovits, U.S. Pat. No. 3,528,428, issued Sept. 15, 1970 for "Demand Pacer" and U.S. Pat. No. 3,766,413, issued Oct. 15, 1973 for "Rate Discrimination Circuit". In these patents a demand pacer is described which, when sensing continuous wave electrical interference signals having a repetition rate much greater than a natural heartbeat repetition rate (for instance, 50 Hz. to 60 Hz. line interference) delivers heart stimulating impulses at its preset rate rather than having its heart stimulating impulses suppressed. In such a pacer the sensed signals are fed, after amplification, to a pulse forming circuit and then to a circuit having a resistive-capacitive (R-C) time constant.

When the time interval between two successive input events is similar to, or larger than, the R-C time constant, a large volage change occurs across the capacitor and it is this large voltage excursion which triggers or resets the pacer pulse generated timing circuit. Where the interval between two successive events is small compared to the R-C time constant, there is little change in the voltage across the capacitor at the occurrence of the second event and too little to trigger or reset the pacer timing circuit. This principle is most effective in preventing dangerous pacer operation in the presence of continuous wave electrical interference. However, the leading edge of the interference can trigger or reset the pacer pulse generator timing circuit once. Thus, if the interfering signal is in the form of short bursts, or is modulated or otherwise fluctuating in mangitude or frequency content, and the rate of the burst or modulation or fluctuation is not short compared to the R-C time constant, then the pacer output can be held suppressed for as long as the interference persists.

A further example of the prior art is a demand pacer which is refractory, that is, inoperative, for the first three-eighths of the pacer pulse generator timing cycle as measured from the last sensed event or delivered heart stimulating impulse. This device is set forth in a Cordis Corporation manual entitled Omni-Stanicor Implantable R-Wave Inhibited Cardiac Pacer in the Programmable Omnicor System, dated November 1972 and specifically pages 11-4 and 11-12 thereof. In this example, at the end of the refractory period is an interference sampling period having the duration of one-sixteenth of the pacer pulse generator timing cycle. During the interference sampling period any input events (voltage fluctuations crossing zero) are counted and, if exceeding a predetermined number (four), the input is classified as interference. The circuitry then, normally active to reset the pacer pulse generator timing cycle is deactivated for the remainder of the timing cycle and the heart stimulating impulse is delivered and the cycle recommenced. The effectiveness of this principle is limited in that interference can only be discriminated against by being detected during the short interference sampling period. Moreover, four or fewer pulses during the sampling period will not be recognized as interference while a pulse or burst outside the narrow sampling period will falsely reset the pulse generator. In other words, the principle is most effective in the presence of continuous wave interference, and only effective in the case of bursts of interference if the bursts coincide with the short interference sampling period.

SUMMARY OF THE INVENTION AND OBJECTS

A principal objective of the present invention is to reduce the probability of demand pacer response to interfering electrical signals, that is, any signal of sufficient magnitude to be sensed by the amplifier of the demand pacer and originating from any source other than a naturally occurring depolarization of the cardiac muscle cells as evidenced cardiographically by that electrical manifestation known in clinical practice as the QRS sector of the cardiogram.

The invention is particularly effective in preventing inhibition of the demand pacer by signals generated by contraction of the skeletal muscles of the patient, such as those referred to in an article entitled "Interference Effects of Myopotentials in Demand Pacers" by O. J. Ohm et al., Brit. Heart Journal, 1974, 36, 77–84.

The pacer includes terminal means which may be connected to a patient's heart, together with means to generate heart stimulating electrical impulses for application to those terminals. Control pulses are derived in response to the appearance at the terminals of signals having a predetermined level which may be generated either by the beating action of the patient's heart or any other signals. Timing means is provided to generate first and second timing pulses having first and second timed periods respectively and in addition, there are means responsive to the control pulses received at the terminals and to the timing means for generating coincidence pulses when the control pulses appear later than the first time period but prior to the end of the second time period. The timing cycle of this heart stimulating electrical impulse generator may be reset in response to the control pulses beginning a new timing cycle prior to its otherwise normal commencement and there are also means responsive to the coincident pulses which will prevent the resetting of the timing cycle.

BRIEF DESCRIPTION OF THE DRAWING

FIG. 1 is a block diagram showing the preferred embodiment of the invention;

FIG. 2 is a schematic diagram showing the invention depicted in FIG. 1; and

FIG. 3 is a partial schematic diagram showing an addition to the circuit of FIG. 2 to provide a further delay.

DETAILED DESCRIPTION OF THE PREFERRED EMBODIMENT

Applicant's investigation and analysis of the characteristics of sensed heartbeat signals, of interfering signals and of demand pacer behavior have led to certain conclusions which form the basis of the present invention. First, the time duration of certain electrical manifestations of a single heartbeat, that is, the QRS of the endocardiogram, never exceeds a certain time period — 60 milliseconds. Secondly, an arbitrary lower limit to the time interval between two natural heartbeats may be assigned. Although somewhat subjective a normal rate for the heart may be assumed at about 70 beats per minute or about 860 milliseconds between pulses. The arbitrary lower limit lies between 30% and 40% of normality or, in the embodiments described herein, about 310 milliseconds.

By combining these two observations, the criteria for providing a degree of discrimination between a sensed natural heartbeat and a sensed interference signal may be established. Any sensed signal occurring later than the first time period (that is, about 60 milliseconds after the immediately preceding sensed signal) but prior to the end of the second time period (that is, about 310 milliseconds after the immediately preceding sensed signal) is classified as interference.

The sensing of any single interference signal implies to a high degree of probability that a second interference signal will follow before the next natural heartbeat. Thus, upon sensing an interference signal, the means normally operative to reset the pacing pulse generator timing circuit should be disabled and held disabled at least until after delivery of the next heart stimulating impulse delivered by the pacer. Moreover, after sensing an interference signal the inhibit function of the pacer is disabled whereby the next available pulse is applied to the heart from the pacer.

As stated above, an arbitrary lower limit may be assigned to the time interval between two natural heartbeats. This time period, of 30% to 40% of the assumed normal heartbeat interval, is measured from the preceding sensed natural heartbeat or delivered heart stimulating impulse. It is not physiologically necessary that a natural heartbeat actually reset the timing circuit of the pacing pulse generator during this period. Thus, by making the pacing pulse generator insensitive to resetting pulses during this period, but maintaining the amplifier and sensing functions operative, any interfering signal can be sensed and discriminated against without resetting the pacing pulse generator timing circuit for 30% to 40% of the timing cycle. This allows a maximum probability of any interference existent to be safely discriminated against. It should be noted, however, that the detection of very large magnitude signals by the sensing amplifier, for example, sensing of the heart stimulating impulse delivered by the pacing pulse generator, will normally paralyze the sensing amplifier for a time period of up to 20% of the pacing pulse generator timing cycle and it will, therefore, be unresponsive to any input signals during this time.

A time delay may be introduced, within physiologically dictated limits, between the instant of sensing a signal from the heart electrodes and the instant of resetting the pacing pulse generator timing cycle. The physiological limit arises because this resetting delay increases the time interval between a sensed heartbeat and a paced heartbeat by the amount of the delay. This constraint limits the period of delay to not greater than some 100 milliseconds for a pacer having a free running pace rate of 70 beats per minute.

This time delay is effective in enhancing interference discrimination in that it allows for some retrospective examination of the validity of any sensed signal.

Referring to the block diagram of FIG. 1, a pulse generator 11 operates continuously and normally provides impulses of 0.5 milliseconds duration at a repetition rate of 70 per minute (860 milliseconds). These pulses are passed to the lower input of an inhibit gate 13. The upper input of the inhibit gate is normally unenergized, under which conditions a facsimile of the impulse from the pulse generator 11 appears at the output of the inhibit gate and is conducted to the pacing output circuit 15 to produce a 6 volt amplitude, 0.5 millisecond duration, heart stimulating impulse which is conducted to the heart through terminal 17. The same electrical connection to the heart allows sensing of naturally occurring heartbeats by an amplifier 19.

The electrical R wave of the heartbeat may have an amplitude as low as 2 millivolts. The function of the amplifier 19 is to increase the magnitude of this R wave signal to a level sufficient that stable detection of signals exceeding a predetermined amplified magnitude may be performed by the comparator 21. The comparator 21 is structured such that an amplifier output excursion of +180 millivolts exceeds the sensing level of the comparator 21, to produce a rectangular output pulse from the comparator of predetermined amplitude and of duration equal to that time period during which the amplifier output excursion exceeds the comparator sensing level.

The output pulse from the comparator 21 comprises a control pulse and is fed to a first timer 23 to produce first timing pulses. To this end the timer 23 begins a predetermined timing period of 60 milliseconds at the leading edge of the comparator 21 output pulse. In the event of the amplifier 19 sensing a plurality of input signals and consequently, causing the comparator 21 to produce a plurality of output pulses, the first timer 23 is activated to begin its timing period at the first of the plurality of pulses and is unresponsive to further pulses provided that the last of the plurality of pulses occurs earlier than the termination of the predetermined timing period of 60 milliseconds.

It should be noted that the function of the first timer 23 may be incorporated within the comparator 21 or the amplifier 19 by various blocking, timing or feedback methods known to those skilled in the art. In the combination of sensed functions, however, care should be taken not to prejudice the primary functions of the comparator 21 or amplifier 19. The initiation of the timing period of the first timer 23 causes a change of state to occur at the upper input of a signal gate 25. The lower input of the signal gate 25 is normally unenergized, under which condition the change of state of the upper input produces a change in state at its output. This change of state is applied to the upper input of the inhibit gate 13 and as a pulse to a refractory control circuit 27.

The function of the refractory control circuit 27 is to provide that a pulse from the output of the signal gate 25 may not reset the timing cycle of the pulse generator 11 earlier than a predetermined time period measured from the beginning of each timing cycle of the pulse generator 11 itself. In this embodiment of the invention the predetermined refractory time is 350 milliseconds. However, a greater or considerably shorter period may be employed including complete elimination of the refractory period. Reduction or complete elimination of the refractory period, however, will cause a consequent degrading of the pacer function.

It should be noted that many heart pacers employ means rendering the sensing amplifier, or following pulse deriving circuitry, refractory for a finite time period after the last sensed signal or heart pacing impulse; that is, the total pacer is insensitive to any events at the electrode during the refractory time. This sensing refractoryness should not be confused with the quite different function of the pacing pulse generator refractoryness of this illustrative embodiment of the invention. In pacing pulse generator refractoryness only the pulse generator itself is refractory while the remainder of the system remains active. Thus, sensed signals may be examined during the refractory period.

Any pulse applied to the refractory control circuit 27 later than 350 milliseconds after the beginning of the timing cycle of the pulse generator 11 resets the pulse generator 11 to begin a new timing cycle, with coincident conduction of an impulse from the output of the pulse generator 11 to the lower input of the inhibit gate 13.

Normally, the upper input of inhibit gate 13 is unenergized and the inhibit gate is in the "pass" condition. Under this condition the impulse from the pulse generator 11 could cause a heart stimulating impulse to be applied to the heart through the terminal 17 by way of the pacing output 15. However, the change of state at the output of signal gate 25 (which was also applied by way of the refractory control 27 to reset the pulse generator 11) is applied to the upper input of the inhibit gate 13 to place that gate in a "no pass" state. Thus, the sensing by the amplifier 19 of a signal exceeding the sensing level of the comparator 21 will cause the pulse generator 11 timing cycle to be reset to begin a new timing cycle without the delivery of a heart stimulating impulse to the heart to the terminal 17, provided that such signal sensed by the amplifier 19 is at a point in time not earlier than the termination of the predetermined refractory period. In this respect the embodiment behaves in the manner of an inhibited demand pacer.

Operation in the manner of a ventricular synchronous demand pacer may be gained by disconnecting the coupling between the output of the signal gate 25 and the upper input of the inhibit gate 13 and by applying a fixed potential at the upper input of the inhibit gate 13 comparable to that normally applied when there is no signal output from the gate 25.

As earlier stated, an output pulse from the comparator 21 sets the first timer 23 to begin a 60 millisecond timing period. During this timing period a change of state exists at the output of timer 23. The input of a second timer 29 is derived from the output of the first timer 23 and the circuit is so structured that termination of the 60 millisecond timing period of the timer 23 causes the timer 29 to begin its timing period to produce a second timing pulse. In this embodiment the timing period of the timer 29 is predetermined at 250 milliseconds, during which period a change of state exists at the output of timer 29 and is applied to the lower input of a coincidence detector 31. Any later changes of state at the output of the first timer 23 have no effect upon the timer 29 unless occurring later than the predetermined 250 millisecond period of the timer 29.

The coincidence detector 31 is so structured that if a change of state occurs at its upper input coincident with the change of state at its lower input, a change of state likewise occurs at its output. Alternative functional configurations of the comparator 21, timer 23 and timer 29 may be employed without departing from the scope of the invention. For example, the output pulses from the comparator 21 may be conducted to the coincidence detector 31 by way of a further gate, such gate activated to be in the "pass" state only during the period of the timer 29. Alternatively, the timer 29 may be activated by the leading edge of a pulse from the comparator 21, rather than the trailing edge of the pulse from the timer 23. Under this latter condition, the predetermined period of timer 29 should be increased by an amount equal to the period of the timer 23 or in the instant embodiment of the invention, to a total timing period of 310 milliseconds.

The upper input of the coincidence detector 31 is derived from the output of the comparator 21. Thus, any output pulse from the comparator at any time during the period of the second timer 29 constitutes coincidence with a consequent change of state at the output of the coincidence detector being applied to set a latch 33. Once set, the latch is so structured as to remain set until reset by the trailing edge of an output pulse from the inhibit gate 13 corresponding to the trailing edge of a heart stimulating impulse through the terminal 17.

However, alternative function configurations may again be employed without departing from the scope of the invention. For example, the latch 33 may be replaced by the monostable timer, as used for the timers 23 and 29, whose timing period is initiated by the output pulse from the coincidence detector. Thus, the signal gate may be held in the "no pass" state for a predetermined time period and not governed by the generation of a pacing output to the heart.

A mixed system may also be employed, in which the timing period during which the signal gate 25 is held in the "no pass" state is again a predetermined timing period unless a pacing output occurs earlier than the normal completion of the predetermined period. Further, the pacing output which terminates the "no pass" status of the signal gate 25 need not necessarily be the next generated pacing output pulse but may be a later pacing output pulse.

The output of the latch 33, which undergoes a change of state when the latch is set, is conducted to the lower input of the signal gate 25 under which condition the signal gate is in the "no pass" state and any change of state at the upper input of the signal gate 25 is not reflected as a change of state at its output.

The timer 23 is structured with two outputs, both undergoing the prestated change of state during the predetermined timing period. However, the two outputs are so structured that the change of state applied to the upper input of signal gate 25 is delayed by a predetermined time period compared to the output applied to the coincidence detector 31 from the comparator 21. Thus, the sensing of the signal by the amplifier 19, producing an output from the comparator 21, later than the termination of the period of the timer 23 and earlier than termination of the period of timer 29 causes the signal gate 25 to prevent this signal, as well as any later signal, from resetting the pulse generator 11 until after that pulse generator has caused the delivery of a heart stimulating impulse through the terminal 17.

The beforementioned delay may be increased, within limits dictated by physiological constraint as related in the above stated criteria, by interposing a further timer in the line to the signal gate 25. The further timer will serve to delay the point in time at which the pulse generator 11 is reset by a signal sensed by the amplifier 19. A practical timer period for this delay is about 100 milliseconds under which condition the heartbeat interval between two paced heartbeats will be the predetermined 860 milliseconds (that is, 70 beats per minute) interval of the timing pulse generator 11 but the heartbeat interval between a sensed heartbeat and a paced heartbeat will be the 860 plus 100 milliseconds or 960 milliseconds (that is, 62.5 beats per minute). This means that the natural rhythm of the patient's heart must fall below 62.5 beats per minute before pacing takes over at 70 beats per minute. This characteristic is considered by many to be physiologically advantageous. Indeed, many pacers are designed to have this "hysteresis" characteristic. But in such instances the hysteresis is ganined by "triggering hysteresis" in the pulse generator rather than by delaying the control pulses from the sensing amplifier function. Such triggering hysteresis, caused by different voltages on the timing capacitor dependent upon whether it is triggered by a control pulse rather than reaching the end of its full timing cycle, or even on the number of full timing cycles preceding the triggered reset, is inherently imprecise and may be confusing to the cardiologist.

The utilization of the 100 millisecond delay allows improved interference discrimination. However, since many physicians prefer a pacer to have no hysteresis the delay may be incorporated or deleted in accordance with individual preference as can be seen by the detailed circuit descriptions which follow. By use of the additional delay, it can be seen that the sensing of a signal later than 60 milliseconds (the period of timer 23) but earlier than 100 milliseconds (the delay period) after the first sensed signal causes the signal gate 25 to prevent both the first and second sensed as well as any later sensed signals, from resetting the pulse generator 11, until after the pulse generator has caused delivery of a heart stimulating impulse to the heart through the terminal 17.

Referring to FIG. 2, a complete electrical schematic of an illustrative embodiment of the invention is shown. A 7 volt battery 35, having a tap at 1.4 volts is employed as the electrical power source of the pacer. A complimentary pulse generator employing transistors 37 and 39, related resistors 41, 43 and 45 and capacitor 47 generates impulses of 0.5 millisecond width at a free running repetition frequency of 70 pulses per minute.

Initially, transistor 39 is forward biased from the 1.4 volt battery tap by way of resistor 41. The emitter of transistor 39 is effectively at zero potential because of the uncharged condition of capacitor 47 and low resistance of resistor 43. As transistor 39 begins to conduct, current begins to be drawn from the 7 volt battery terminal (hereinafter referred to as V+) through the emitter-base junction of the transistor 37 to forward bias the transistor 37. The mutual effect is for transistors 37 and 39 to forward bias each other in an avalanching manner so that a pulse of current flows from V+ through transistors 37 and 39 and resistor 43 to charge the capacitor 47. As the voltage across capacitor 47 rises, at a rate determined by the capacitor 47 and the time constant resistance 43, the voltage at the emitter of transistor 39 rises toward its base voltage until the forward bias is insufficient to maintain its collector current and mutual degeneration between transistors 37 and 39 terminates the charging of capacitor 47. A rectangular voltage pulse rising from 1.4 volts to nearly V+ and of a duration essentially determined by the time constant of resistor 43 and capacitor 47 is thus seen at the collector of transistor 37. The charge of capacitor 47 then leaks away through resistors 43 and 45 at a rate determined by the time constant of the resistor 45 and capacitor 47 until transistor 39 again begins to be forward biased and the cycle is repeated.

A NAND gate 49 is inverter connected so that its output is normally at logic level 1, falling to logic level 0 during each impulse from the pulse generator. The upper input of a NOR gate 51 is normally at logic level 0, thus, the logic level 0 pulse at the lower input of gate 51 produces a logic level 1 pulse at its output. This pulse is conducted by way of resistor 53 to forward bias a pacing output transistor 55. With transistor 55 normally in its off state, capacitor 57 charges from V+ through resistor 59 and the heart electrodes 61 and 63. The forward biasing pulse applied to transistor 55 thus causes a voltage pulse to be applied to the heart electrodes 61 and 63 from the capacitor 57 by way of the collector emitter junction of transistor 55.

Amplifier 65, by way of capacitor 67 to the negative heart electrode 61 and referenced to the negative battery terminal, functions to amplify the low level signals of a naturally occurring heart beat. The amplifier 65 is a programmable monolithic operational amplifier with resistor 69 determining its operating current. From the output of amplifier 65, resistor 71 provides stabilizing dc feedback to the inverting input while capacitors 73 and 75 and resistor 77 shape the ac feedback characteristic such that amplifier gain is maximum for signals in the 30 to 50 hertz region. The dc working voltage level of amplifier 65 is determined by the resistive voltage chain comprising resistors 79, 81 and 83 from which the voltage at the junction of resistors 81 and 83 is applied by way of resistor 85 to the noninverting input of amplifier 65. Note that the same voltage divider chain 79, 81 and 83 is also employed to determine the sensing level of a comparator 87.

The comparator 87 is another operational amplifier identical to amplifier 65 but operated in open loop mode. Resistor 89, by way of resistor 69, determines the operating current level. The noninverting input of comparator 87 is directly coupled to the output of amplifier 65. The inverting input of the comparator 87 is connected by way of resistor 91 to the junction of resistors 79 and 81 of the voltage divider chain. With this configuration, with no signal being sensed by the amplifier 65, there is a voltage difference of +180 millivolts at the inverting input of the comparator 87 referred to the noninverting input and thus the output of the comparator 87 will be resting at near zero potential, that is at logic level 0. Upon sensing of a signal by the amplifier 65 of such magnitude and polarity that the output of amplifier 65 swings positive by more than 180 millivolts, the polarity of the inputs to the comparator 87 will be reversed producing a logic level 1 pulse at its output. Note that in this embodiment a single sided comparator 87 is employed sensing only positive amplifier excursions. Amplifier 65 differentiation permits both negative and positive signals at the amplifier to be sensed with some asymmetry. A dual comparator may be used for greater symmetry without altering the operating principle of the embodiment.

Following the comparator 87 is a first timer comprised of NOR gate 93 operating in conjunction with amplifier 95 and associated components. As before, the working current level of the operational amplifier is determined by a program resistor 97. The amplifier 95 is operated as an open loop comparator with its noninverting input set to one-half V+ by the voltage divider network employing resistors 99 and 101. The output of the comparator 87, normally at logic level 0, is coupled by capacitor 103 to the upper input of NOR gate 93. The inverting input of the amplifier 95 is biased by way of resistor 105 to a higher voltage level than its noninverting input and thus the output of amplifier 95 sits at logic level 0. This logic level 0 is directly coupled to the lower input of NOR gate 93. The upper input of NOR gate 93 is held normally at logic level 0 by resistor 107 under which condition the output of NOR gate 93 sits at logic level 1.

Upon the occurrence of a pulse at the output of comparator 87, coupled by capacitor 103, the output of NOR gate 93 switches to logic level 0 and by way of capacitor 109, the polarity of the inverting input of amplifier 95 is reversed thus changing the output of amplifier 95 to logic level 1. The direct coupling of the output of amplifier 95 to the lower input of the NOR gate 93 thus holds the output of NOR gate 93 at logic level 0 after the termination of the initiating pulse from the comparator 87 and for a time period determined by the charging time constant of capacitor 109 and resistor 105. As capacitor 109 charges, the potential at the inverting input of amplifier 95 rises until it is greater than the potential at the junction of resistors 99 and 101 upon which the output of amplifier 95 reverts to logic level 0 and consequently, the output of NOR gate 93 reverts to the logic level 1 signifying the end of the 60 millisecond timing period. With the output of NOR gate 93 at logic level 1, capacitor 109 is rapidly discharged to V+ through diode 111 and the timer is ready for retriggering by any further pulse from the comparator 87.

As previously stated, upon occurrence of an output pulse from the comparator 87, NOR gate 93 is first switched and then initiates the switching of amplifier 95. Thus, while the outputs of both NOR gate 93 and amplifier 95 undergo a change of state during the 60 millisecond timing interval, the timing pulse seen at the output of the amplifier 95 is slightly delayed by the slewing rate limitations of the amplifier itself. This delay is utilized to allow the succeeding logic circuitry time to act upon an output pulse from the comparator 87 and block its transmission to the pacing circuitry. However, the NOR gate 113 which normally receives the output of the amplifier 95, may be deleted and by coupling the upper input of the NOR gate 115 directly to the output of NOR gate 93, the correct logic levels are preserved and the prestated delay not utilized. However, there will be a penalty of some reduction in the interference discrimination of the pacer.

Conversely, the interference discrimination of the pacer may be improved further by providing a delay longer than that attainable by the slewing rate limitation of the amplifier 95 between the occurrence of a pulse at the output of comparator 87 and the time of application of a control pulse to the upper input of the gate 115. This longer delay may be incorporated in a manner shown in FIG. 3 to be discussed later.

In the normal "demand " function of the pacer the change of state at the output of amplifier 95, from logic level 0 to logic level 1 upon a pulse from the comparator 87, is applied to the NOR gate 113 which acts as an inverter. The output of the gate 113 is direct coupled to the upper input of the NOR gate 115. This input is normally at logic level 1 switching to logic level 0 at the onset of the 60 millisecond timing interval. The lower input of the NOR gate 115 is normally at logic level 0 under which condition the output of gate 115 switches from logic level 0 to logic level 1 upon switching of its upper input from logic level 1 to logic level 0. The output of NOR gate 115 is coupled by way of capacitor 117 and resistor 119 to the bias point of the pulse generator comprising the PNP transistor 37 and NPN transistor 39. In addition, the output of NOR gate 115 is direct coupled to the upper input of NOR gate 51.

When the output of NOR gate 115 switches from logic level 0 to logic level 1, a positive pulse by way of capacitor 117 and resistor 119 drives the bias point positive to cause the pulse generator to reset and begin a new timing cycle. The voltage magnitude of the resetting inpulse applied to the bias point of transistors 37 and 39 determines how early the pulse generator timing cycle may be reset as measured from the beginning of the cycle. It should be recognized that the bias point must be driven sufficiently higher than the instantaneous exponentially decaying voltage at the emitter of transistor 39 in order to forward bias that transistor and initiate the avalanche switch on of transistors 37 and 39. This control of the magnitude of the resetting pulse voltage is preformed by the divider resistor 119 in conjunction with the biasing resistor 41. In this embodiment of the invention, the value of resistor 119 is chosen such that the pulse generator cannot be reset earlier than 350 milliseconds into its cycle, keeping in mind that the free running cycle time is 860 milliseconds.

At the same time that the pulse generator is reset by the logic level 1 pulse from NOR gate 115, the state of the upper input of NOR gate 51 is reversed from its normal logic level 0 to logic level 1. This reversal puts the gate 51 in the "no pass" state for a pulse arriving at its lower input from the NAND gate 49 consequent upon resetting of the pulse generator comprising the transistors 37 and 39. Thus, a sensed heartbeat resets the timing cycle of the pulse generator without the pacing output transistor 55 being switched to produce a pacing output.

The circuit may be made to operate alternatively as a ventricular synchronized pulse generator by deleting the coupling from the output of NOR gate 115 to the input of NOR gate 51 and by biasing the upper input of NOR gate 51 to hold it at logic level 0.

As previously stated, the output of NOR gate 93 undergoes a change in logic level from 1 to 0 for 60 milliseconds after the onset of a pulse from the comparator 87. The output of NOR gate 93 is direct coupled to the upper input of NOR gate 121 which, in association with the comparator 123 and associated components, forms a second timer having a timing period of 250 milliseconds. This second timer is electrically identical in function to the first described timer except for the increased time constant of the capacitor 125 and resistor 127 necessary to yield the 250 millisecond timing period.

During the 60 millisecond timing period of the first timer, the upper input of NOR gate 121 is at logic level 0. At the termination of the 60 millisecond timing interval of the first timer that input switches to logic level 1 and initiates the 250 millisecond timing period of the second timer.

The output of comparator 123, which is direct coupled to the upper input of NAND gate 129, is normally at logic level 0 switching to logic level 1 during the 250 millisecond timing period of the second timer. The lower input of NAND gate 129 is normally at logic level 0 switching to logic level 1 upon an output pulse from the comparator 87. With either input of the NAND gate 129 at logic level 0 its output is at logic level 1. However, should the inputs at any time both attain a logic level 1 status the output of NAND gate 129 switches to logic level 0. Thus, an output pulse from the comparator 87 at any time during the 250 millisecond timing period of the second timer causes a change in state in the output of NAND gate 129 from logic level 1 to logic level 0.

NAND gates 131 and 133 constitute a bistable latch. With the application of a logic level 0 pulse from the NAND gate 129 the output of gate 131 is set to logic level 1. The lower input of NAND gate 133 is connected to V+ through the resistor 135. Thus, the application of a logic level 1 output pulse from the NAND gate 131 to the upper input of NAND gate 133 causes the output of gate 133 to assume logic level 0 which is applied to the input of NAND gate 131 to maintain the latch so long as the lower input of NAND gate 133 remains at logic level 1. A logic level 0 pulse from the input of NOR gate 51 (that is, at the trailing edge of a positive output pulse from the gate 51) will set the output of gate 133 to logic level 1. If the logic level 0 pulse from gate 129 has ended, the output of gate 131 will then switch to the logic level 0. The output of NAND gate 131 is directly coupled to the lower input of NOR gate 115.

With the latch set such that the output of NAND gate 131 is at logic level 0, the NOR gate 115 is, as earlier stated, in the "pass" condition and the timing cycle of the pulse generator comprising transistors 37 and 39 may be reset by way of capacitor 117 and resistor 119.

However, upon coincidence of logic level 1 at both inputs of NAND gate 129, the output of gate 129 switches from logic level 1 to logic level 0 and reverses the state of the latch so that the NOR gate 115 is placed in the "no pass" state. Thus, any pulse from the comparator 87 occurring later than the termination of the 60 millisecond timing period of the first timer and earlier than termination of the 250 millisecond, timing period of the second timer causes the NOR gate 115 to prevent resetting of the timing cycle of the pulse generator comprising transistors 37 and 39 by this or any later pulse from the comparator 87. The NOR gate 115 prevents resetting of the pulse generator until the state of the latch is reversed. This reversal of the latch is caused by a change from logic level 1 to logic level 0 at the lower input of gate 133 derived from the output of NOR gate 51 coincident with the trailing edge of a heart stimulating inpulse from the transistor 55 and capacitor 57 to the heart electrodes 61 and 63.

In the embodiment of the invention shown in FIG. 2 various components employed have the values and type identification set forth below in Table No. I. The amplifiers set forth in Table No. I, as well as those in Table No. II, are identified by numbers employed by their manufacturer, Fairchild Semiconductor of Mountain View, California. Similarly, the gates are as identified by their manufacturer, Motorola Semiconductors Inc., of Phoenix, Arizona.

TABLE I

| Amplifiers | |
|---|---|
| 65 | Operational Amplifier µA776 |
| 87 | Operational Amplifier µA776 |
| 95 | Operational Amplifier µA776 |
| 123 | Operational Amplifier µA776 |
| Gates | |
| 49 | ¼ of 74C00 NAND gate (C MOS) |
| 51 | ¼ of 74C02 NOR gate (C MOS) |
| 93 | ¼ of 74C02 NOR gate (C MOS) |
| 113 | ¼ of 74C02 NOR gate (C MOS) |
| 115 | ¼ of 74C02 NOR gate (C MOS) |
| 121 | ¼ of 74C02 NOR gate (C MOS) |
| 129 | ¼ of 74C00 NAND gate (C MOS) |
| 131 | ¼ of 74C00 NAND gate (C MOS) |
| 133 | ¼ of 74C00 NAND gate (C MOS) |
| Transistors | |
| 37 | Transistor BC177 |
| 39 | Transistor BC109 |
| 55 | Transistor BC109 |
| Diodes | |
| 111 | Diode OA202 |
| 137 | Diode OA202 |
| Capacitors | |
| 47 | Capacitor 0.1 µfd |
| 57 | Capacitor 10 µfd |
| 67 | Capacitor 0.022 µfd |
| 73 | Capacitor 220 pf |
| 75 | Capacitor 0.1 µfd |
| 103 | Capacitor 0.001 µfd |
| 109 | Capacitor 0.033 µfd |
| 117 | Capacitor 470 pf |
| 125 | Capacitor 0.047 µfd |
| 145 | Capacitor .001 µfd |
| 149 | Capacitor .001 µfd |
| 151 | Capacitor 33 µfd |
| Resistors | |
| 41 | Resistor 27K ohm |
| 43 | Resistor 560 ohm |
| 45 | Resistor 4.7M ohm |
| 53 | Resistor 47K ohm |
| 59 | Resistor 10K ohm |
| 69 | Resistor 15M ohm |
| 71 | Resistor 2.7M ohm |

TABLE I-continued

| | |
|---|---|
| 77 | Resistor 15K ohm |
| 79 | Resistor 2.2M ohm |
| 81 | Resistor 180K ohm |
| 83 | Resistor 4.7M ohm |
| 85 | Resistor 1.5M ohm |
| 89 | Resistor 10K ohm |
| 91 | Resistor 680K ohm |
| 97 | Resistor 22M ohm |
| 99 | Resistor 10M ohm |
| 101 | Resistor 10M ohm |
| 105 | Resistor 3.3M ohm |
| 107 | Resistor 2.2M ohm |
| 119 | Resistor 47K ohm |
| 127 | Resistor 10M ohm |
| 135 | Resistor 470K ohm |
| 139 | Resistor 10M ohm |
| 141 | Resistor 10M ohm |
| 143 | Resistor 22M ohm |
| 147 | Resistor 470K ohm |

Referring now to FIG. 3, the additional timing function referred to hereinabove is illustrated whereby interference discrimination capability is further increased.

FIG. 3 is but a partial schematic with components additional to those described in FIG. 2 being shown in solid lines. Components which are identical to those of FIG. 2 are shown in dashed lines to assist in locating the additional circuitry.

The NOR gate 113 of FIG. 2 is not used in the embodiment of FIG. 3, its inverting function being performed by the overall timer shown in solid lines in FIG. 3. The output of amplifier 95, normally at logic level 0 and switching to logic level 1 upon an output pulse from a comparator 87 is applied to the upper input of NOR gate 153. The lower input of NOR gate 153 is normally at logic level 0, being derived from the output of comparator 155 whose noninverting input is biased by way of resistor 157 to a higher voltage than the one-half V+ potential applied to the inverting input by means of the voltage divider comprising resistors 159 and 161. Thus, the output of the NOR gate 153 is normally at logic level 1.

Upon an output pulse from the comparator 87 the upper input of NOR gate 153 switches to logic level 0 and by way of capacitor 163 the noninverting input of comparator 155 is switched to logic level 0. This causes the output of comparator 155 to switch to logic level 1 so as to hold the lower input of NOR gate 153 at logic level 1 and thus its output at logic level 0. As the capacitor 163 charges by way of resistor 157, the voltage at the noninverting input of the conparator 155 rises until it exceeds the one-half V+ voltage at the inverting input. At this point the output of the comparator 155 reverses thereby reversing the output of the NOR gate 153 and terminating the 100 millisecond timing period. With the output of NOR gate 153 now at logic level 1 capacitor 163 is rapidly discharged through the diode 165 to V+.

Thus, upon an output pulse from the comparator 87 the output of comparator 155 attains a logic level 1 for the predetermined period of 100 milliseconds.

The upper input of gate 115 is held normally at logic level 1 by reason of its connection to V+ through resistor 167 and this status is unaltered by the onset of the timing pulse at the output of the comparator 155. However, at the end of this timing period, the output of the comparator 155 switches to logic level 0 which pulls the upper input of NOR gate 115 to logic level 0 for a time period determined by the time constant set by the resistor 167 and capacitor 169. In this illustrative embodiment of the invention the resistor 167 and capacitor 169 are chosen such as to produce a 2 millisecond pulse at the output of gate 115 when gate 115 is in the "pass" condition.

It can thus be seen that a delay of 100 milliseconds is introduced between the instant that a sensed input pulse produces an output from conparator 87 and the instant the timing is reset for the pacemaker pulse generator comprising transistors 37 and 39. Therefore, any input event occuring later than 60 milliseconds after the last sensed event, but earlier than 100 milliseconds, causes the latch comprising gates 131 and 133 to be activated thereby disabling gate 115 to prevent resetting of the pacing pulse generator not only by the second sensed and later sensed input events but also by the first sensed event itself.

When the delay circuit of FIG. 3 is employed those components in addition to the ones set forth in FIG. 2 have values and type identifications as described in Table II below.

TABLE II

| Amplifiers | |
|---|---|
| 155 | Operational Amplifier $\mu$A776 |
| Gates | |
| 153 | ¼ of 74CO2 NOR gate (C MOS) |
| Diodes | |
| 165 | Diode OA202 |
| Capacitors | |
| 163 | Capacitor 0.047 $\mu$fd |
| 169 | Capacitor 0.001 $\mu$fd |
| Resistors | |
| 157 | Resistor 3.3M ohm |
| 159 | Resistor 10M ohm |
| 161 | Resistor 10M ohm |
| 167 | Resistor 2.2M ohm |
| 171 | Resistor 22M ohm |

What is claimed is:

1. A heart pacer comprising terminal means for connection to a patient's heart, free running pulse generating means for generating heart stimulating electrical impulses and for applying said impulses to said terminal means, means for deriving control pulses in response to the appearance on said terminal means of signals above a predetermined level generated by the beating action of said patient's heart and to other signals, timing means responsive to said control pulses for generating first and second timing pulses of first and second predetermined time periods, means responsive to said control pulses and to said timing means for generating coincidence pulses when said control pulses occur after said first predetermined time period but prior to completion of said second predetermined time period, timing reset means responsive to said first timing pulses to reset the timing cycle of said heart pulse generating means to begin a new timing cycle prior to the normal commencement of a new timing cycle, and means responsive to said coincidence pulses for preventing operation of said timing reset means.

2. A pacer in accordance with claim 1 wherein said timing reset means includes means operable upon resetting the timing cycle of said pulse generator means to prevent said pulse generating means from applying a heart stimulating electrical impulse to said terminal means.

3. A pacer in accordance with claim 1 wherein said first predetermined time period is greater than the time period between the first and last of said control pulses derived in response to the appearance on said terminal means of the QRS signal of a single heartbeat.

4. A pacer in accordance with claim 1 wherein said means deriving control pulses includes frequency discrimination means for enhancing the sensitivity of said means to signals of frequencies representative of the heartbeat QRS frequencies appearing on said terminal means.

5. A pacer in accordance with claim 1, together with means for delaying the application of said control pulses to said timing reset means until after application of the control pulses to said timing means.

6. A pacer in accordance with claim 5 wherein said means for delaying the application of said control pulses includes means for delaying said pulses for a period less than said first predetermined time period.

7. A pacer in accordance with claim 5 wherein said means for delaying the application of said control pulses includes means for delaying said pulses for a period greater than said first predetermined time period but less than said second predetermined time period.

8. A pacer in accordance with claim 1 wherein the said second time period is less than the time period between two natural heartbeats.

9. A pacer in accordance with claim 1 wherein the sum time period of said first predetermined time period plus said second predetermined time period is less than the time period between two natural heartbeats.

10. A pacer in accordance with claim 1 wherein the completion of said first predetermined time period initiates the timing of said second predetermined time period.

11. A pacer in accordance with claim 1 wherein said timing means includes means responsive to the leading edge of the first occurring of said derived control pulses for initiating the generation of said first timing pulse and means responsive to the trailing edge of the first occurring of said derived control pulses for initiating the generation of said second timing pulse.

12. A pacer in accordance with claim 1, together with timing means, operable in addition to said means responsive to said coincidence pulses, for preventing operation of said timing reset means over a predetermined time period.

13. A pacer in accordance with claim 12 wherein said means responsive to coincidence pulses includes means for preventing operation of said timing reset means for a predetermined time period.

14. A pacer in accordance with claim 12 wherein said means responsive to coincidence pulses includes means for preventing operation of said timing reset means until a heart stimulating electrical pulse is generated by said pulse generating means.

15. A pacer in accordance with claim 1 wherein said means responsive to coincidence pulses includes means for preventing operation of said timing reset means for a predetermined time period.

16. A pacer in accordance with claim 1 wherein said means responsive to coincidence pulses includes means for preventing operation of said timing reset means until a heart stimulating electrical pulse is generated by said pulse generating means.

17. A pacer in accordance with claim 1 together with refractory means coupled to said pulse generating means for preventing the resetting of the timing cycle of said heart pulse generating means earlier than a predetermined time period after the commencement of said timing cycle.

18. A heart pacer comprising terminal means for connection to a patient's heart, free running pulse generating means for generating heart stimulating electrical impulses and for applying said impulses to said terminal means, means for deriving control pulses and first timing pulses in response to the appearance on said terminal means of signals above a predetermined level generated by the beating action of said patient's heart and to other signals, timing means responsive to said control pulses for generating second timing pulses, said first and second timing pulses respectively, having first and second time periods, means responsive to said control pulses and said timing pulses for generating coincidence pulses when said control pulses occur after said first predetermined time period but prior to completion of said second predetermined time period, timing means responsive to said first timing pulses to reset the timing cycle of said heart pulse generating means to begin a new cycle prior to the normal commencement of a new timing cycle, and means responsive to said coincidence pulses for preventing operation of said timing reset means.

* * * * *